(12) United States Patent
Wallace

(10) Patent No.: US 6,496,732 B1
(45) Date of Patent: Dec. 17, 2002

(54) INTERNAL CARDIAC OUTPUT MONITOR

(75) Inventor: Arthur Wallace, San Rafael, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/578,374

(22) Filed: May 25, 2000

(51) Int. Cl.[7] .............................. A61N 1/36; A61B 5/04
(52) U.S. Cl. ......................... 607/24; 607/9; 600/513; 600/508
(58) Field of Search ............... 607/9, 24, 28; 600/508, 513, 526, 547, 527

(56) References Cited

U.S. PATENT DOCUMENTS

| | | | | |
|---|---|---|---|---|
| 4,450,527 A | * | 5/1984 | Sramek | 600/484 |
| 4,836,214 A | * | 6/1989 | Sramek | 600/506 |
| 4,898,176 A | * | 2/1990 | Petre | 600/374 |
| 5,203,344 A | * | 4/1993 | Scheltinga et al. | 600/547 |
| 5,626,624 A | * | 5/1997 | Schaldach et al. | 607/24 |
| 5,782,774 A | | 7/1998 | Shmulewitz | 600/547 |
| 5,791,349 A | | 8/1998 | Shmulewitz | 600/547 |
| 6,186,955 B1 | * | 2/2001 | Baura | 600/526 |
| 6,287,263 B1 | * | 9/2001 | Briskin | 600/526 |

OTHER PUBLICATIONS

Wallace, M.D., Ph.D., Arthur W.; Salaheih, B§., Ali; Lawrence, BS, Andrew; Spector, MS, M.B.A., Ken; Owens, MS, M.B.A., Chris; Alonso, BS, David; "Endotracheal Cardiac Output Monitor"; *Anesthesiology*, vol. 92, No. 1, Jan. 2000.

* cited by examiner

*Primary Examiner*—Carl Layno
(74) *Attorney, Agent, or Firm*—Greenberg Traurig, LLP

(57) ABSTRACT

Determining the cardiac output of a patient uses first and second electrodes disposed with the peri-aortic adventitia or fat pad of the patient. Third electrode is disposed on the cardiac atrial area of the patient. Fourth electrode is placed either externally on the body surface or internally superior to electrodes one and two. A bioelectrical impedance recorder is coupled to the third and fourth electrodes to pass a current between the electrodes. A bioimpedance recorder is coupled to the first and second electrodes to measure the resulting voltage. The output of the bioelectrical impedance recorder is processed to compute a metric corresponding to the patient's cardiac output. The third electrodes are adapted to be the cardiac pacing electrodes.

39 Claims, 3 Drawing Sheets

INTERNAL CARDIAC OUTPUT MONITOR

BACKGROUND OF THE INVENTION

This invention relates to the monitoring of cardiac output, which can be critical in a post-cardiac surgery patient. Detection, diagnosis, and treatment of volume depletion, tamponade, and ventricular failure can be life-saving.

The measurement of cardiac output can be critical to patient care. 500,000 patients undergo cardiac surgery each year, and many of these patients receive pulmonary artery catheters to aid in hemodynamic management. There have been numerous efforts to replace the pulmonary artery catheter as the gold standard for measurements of cardiac output. Most of these techniques are inaccurate, expensive, or unreliable.

One of these, the Thoracic Electrical Bioimpedance (TEB) has never caught on because of a poor signal-to-noise ratio, low accuracy, and poor reliability. The electrical signal used for TEB is produced by variations in the volume of conductor in the chest. Unfortunately, measurement of the impedance of the chest relies on an accurate knowledge of the current path and associated electrical impedance of structures between the electrodes and the structure changing in volume. Fluid content of the lungs will effect the current path and consequently the magnitude of measured voltages. Cardiac pathology can affect right and left ventricular volumes and produce inaccuracies in the measurement.

Traditionally, TEB signals were thought to derive solely from changes in conductor volume. However, changes in the flow of conducting fluids with no change in conductor volume can effect impedance of that fluid. Flow measurements based on a change in conductor volume are critically dependent on mechanical distensibility of the structure containing the flow. If the mechanical distensibility is nonlinear (as in the aorta or heart) with pressure changes, the accuracy of the flow measurement will suffer over a wide range of pressures and flows. If the flow measurement is based on a true change in flow, the mechanical distensibility of the structure does not matter.

External thoracic electrodes for the measurement of thoracic impedance have been used for years but are not accurate or reliable. Intravascular recordings of left ventricular volume have been made but are highly invasive and only appropriate for animal or small clinical studies. Esophageal measurements have been made but had not been sufficiently accurate.

Endotracheal measurements were hypothesized by Ascher Schmulowitz, U.S. Pat. Nos. 5,782,774 and 5,791,349, the contents of which are incorporated by reference herein. This technology was further described in Wallace et al, Endotrachael Cardiac Output Monitor. *Anesthesiology*, Vol 92 No 1, p178–189, January 2000. The content of that article is also incorporated by reference herein. The Endotracheal Cardiac Output Monitor is termed the ECOM.

At the present time, the pulmonary artery catheter is the most commonly used reliable device for the measurement of cardiac output. Placement of a pulmonary artery catheter is expensive and has associated risk including: death; infection; hemorrhage; arrhythmias; carotid artery; thoracic duct, vena caval, tracheal, right atrial, right ventricular, mitral and tricuspid valvular, and pulmonary artery injury. Little evidence suggests that placement of a pulmonary artery catheter improves survival, and several suggest an increase in morbidity and mortality.

A simple, inexpensive, reliable method for the measurement of cardiac output without the associated risks and costs of a pulmonary artery catheter would be useful.

SUMMARY OF THE INVENTION

An object of the invention is to provide a method and system for the measurement of cardiac output which minimizes the disadvantages of prior art techniques.

According to the invention, there is provided an internal cardiac output monitor system, apparatus, and method (ICOM) for use in cardiac surgery patients who have temporary cardiac pacing in place, namely the pacing electrodes. Two extra wires or leads, namely first and second electrodes, are placed in relationship in the peri-aortic adventitia or fat pad. An alternating electrical current (100 kHz 2 ma) is injected from the atrial pacing wires or leads, namely the third electrode to a ground electrode (fourth). Impedance measurements are taken directly from the aorta. These measurements have a signal-to-noise ratio that is more accurate than extra-thoracic measurements. The current path is limited and relatively insensitive to changes in lung water. The changes in impedance caused by flow can be measured essentially directly. The voltage changes are induced primarily by blood flow dynamics since the current conducted between electrodes flows primarily through high-conductivity blood.

When the temporary pacing wires or leads are removed on postoperative day 4 or 5, the two extra wires or leads for the ICOM are removed at the same time. This system allows inexpensive, reliable, accurate measurement of cardiac output in postoperative cardiac patients for 4 to 5 days with minimal risk. It takes less time to place, is safer, and is less expensive than a pulmonary artery catheter.

The ICOM system is an inexpensive, accurate, reliable system to directly measure aortic impedance and derive cardiac output measurements in post-cardiac surgery patients. The placement of the two extra wires or leads in the peri-aortic adventitia or fat pad provides for accurate functioning. These wires should be separated by at least 10 mm. Both or either orthogonal-to-flow and/or parallel-to-flow placement can be used. Placement orthogonal-to-flow is superior. The impedance measurement circuit should be able to measure a delta Z signal with about 1% accuracy with a Zo of 1 ohm.

The ICOM technique controls the injected current path and measures the changes in impedance of a simple structure to produce a more reliable cardiac output measurement. This technique which increases the signal-to-noise ratio by 100 reduces the electronics cost and makes the technique more commercially viable.

The foregoing and other objects, features, and advantages of the present invention will be apparent from the following detailed description of the preferred embodiments which makes reference to the figures.

DETAILED DESCRIPTION OF THE PREFERRED EMBODIMENT

Figure 1A:
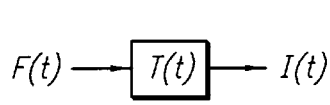
FIGS. 1A and 1B are idealized models of the volumes upon which previously known bioelectrical impedance algorithms are based.

In the following description of the preferred embodiments reference is made to the accompanying drawings which form the part thereof, and in which are shown by way of illustration of specific embodiments in which the invention may be practiced. It is to be understood that other embodiments may be utilized and structural and functional changes may be made without departing from the scope of the present invention.

Apparatus for determining the cardiac output of a patient comprises first and second electrodes 20a and 20b adapted to be disposed in close relationship with the ascending aorta, namely with the peri-aortic adventitia or fat pad of the patient. Third electrode 22a or 22b is adapted to be disposed on the cardiac atrial area of the patient. The third electrode 22a or 22b is conveniently one of the cardiac pacing electrodes. Each of the first and second electrodes 20 and 20b and the third electrode (22a or 22b) and fourth electrode 14 include respectively wires connected to the respective electrodes. The voltage is applied between the third electrode (22a or 22b) and the fourth electrode 14. The voltage developed across the first electrodes 20a and 20b is continuously detected.

There is also a pacemaker 15 for controlling the heart rate of the patient. This pacemaker is routinely used post cardiac surgery. The pacemaker 15 can coupled to the means for processing and be responsive to the metric corresponding to the cardiac output. This system will not interfere with the pacemaker 15 which is electrically coupled through the third electrodes (22a and 22b) as well as (24a and 24b) to the heart of the patient to control heart rate. As an alternative embodiment, the system can adjust the heart rate responsive to voltage developed across the first and second electrodes 20a and 20b to optimize cardiac output. Adjusting the pacing rate may be used to optimize the cardiac output to predetermined levels. The pacemaker is also connected with pacing leads to the ventricle through electrodes 24a and 24b for ventricular pacing.

In an alternative embodiment, the sense electrodes 20a and 20b can be placed parallel to flow along the axis of the aorta. FIG. 3b shows the configuration with electrodes 26a and 26b which are placed in the peri-aortic adventitia or fat pad. The prior configuration with electrodes orthogonal flow 20a and 20b requires different algorithm settings to the parallel configuration 26a and 26b. Having both orthogonal and parallel electrodes increases the accuracy but complicates the implementation by requiring additional electrodes. In an alternative embodiment the electrodes are dual lead electrodes with two elements each. In this embodiment placing a pair of dual lead electrodes would provide the orthogonal and parallel electrodes.

The fourth electrode 14 can be coupled to the bioelectrical impedance recorder 16 and adapted to be disposed on the skin of the thorax in the vicinity of the suprasternal notch or as an internal electrode placed distally on the ascending aortic adventitia, pleura, or great vessel adventitia.

A bioelectrical impedance recorder is coupled to the third and fourth electrodes (22a or 22b) and 14 to pass a current. Additionally it is coupled to electrodes 20a and 20b to measure the voltage produced. If parallel electrodes are used then 26a and 26b would be the measurement electrodes. There are means for processing the output of the bioelectrical impedance recorder 16 to computer a metric corresponding to the patient's cardiac output. This includes circuitry for digitizing the output of the bioelectrical impedance recorder 16.

In different embodiments there can also be a fluid administration system for injecting a bolus of fluid in the vascular system of the patient is coupled to the means for processing and responsive to the metric corresponding to the cardiac output. Periodically, the fluid administration system is actuated on responsive to the detected voltage developed across the first and second electrodes. This periodic actuation is performed periodically only while the cardiac output is measured to be increasing.

In FIG. 1A, a BIA (Bioimpedance Algorithm) algorithm is illustrated. Cardiac output is estimated from the bioelectrical impedance measurement I(t), where it is assumed that changes in the bioelectrical impedance coincidental with the heart electrical activity are the result of blood flow F(t). A transfer function T(t) is then based upon empirical formulae derived from measurements taken on healthy, hemodynamically stable subjects. The bioelectrical impedance is then computed as:

$$I(t)=T(t)*F(t)+N(t) \tag{1}$$

where N(t) is noise.

Figure 1B:
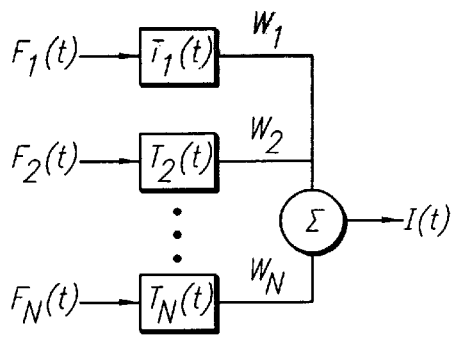

In FIG. 1B, the thoracic approach to BIA measurement accounts for transfer functions appropriate to each of the multiple blood flow paths through the volume:

$$I(t)=F_i(t)*T_i(t)*W_i+N(t) \tag{2}$$

where $W_i$ are weights corresponding to a priori knowledge of the relative distribution of flow through the various segments of the volume, e.g., the aorta, and arterial segments and other fluid chambers. The weights $W_i$ may be different for different patients, may be different for chronically ill as opposed to healthy subjects, and may be variable even within a given patient, e.g., due to changes in heart rate.

Equation (1) can be used accurately for any patient provided that the transfer function T(t) is correlated to measured blood flow (e.g., using a flow meter) where the effect of the distribution weights $W_i$ can be essentially eliminated. The BIA measurements should be taken close to a blood vessel, so that between the electrodes of the BIA apparatus there are no branching vessels or adjacent vessels.

The present invention involves the use of BIA measurements in the vicinity of the ascending aorta, preferably the peri-aortic adventitia or fat pad of the patient.

Figure 2A:
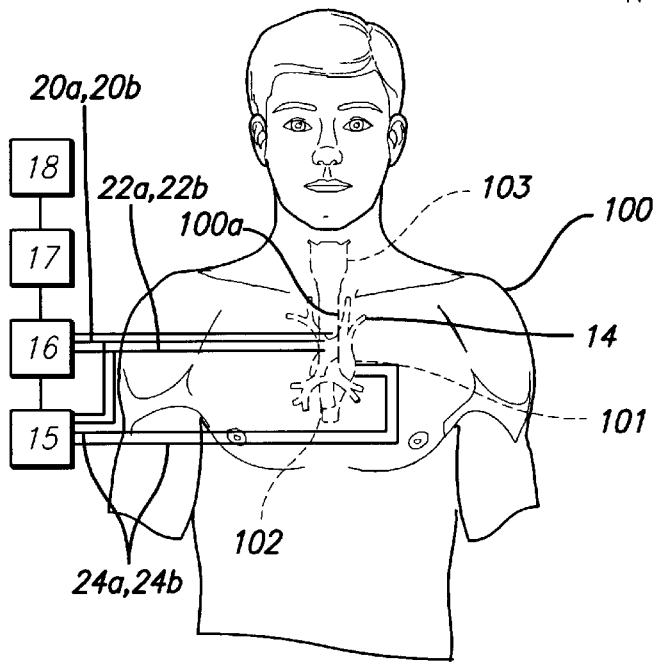
FIGS. 2A and 2B are a vertical frontal view of the upper portion of a human body and a front view of the ascending aorta, the esophagus and the trachea, respectively.
Figure 2B:
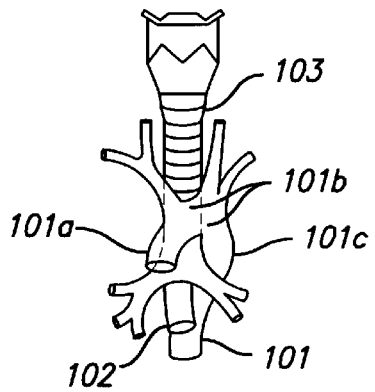

In FIG. 2A, the upper portion of a human body 100 is shown, with the corresponding location of the aorta 101, esophagus 102 and trachea 103 shown in dotted line. These vessels and organs are more clearly depicted in FIG. 2B. The outflow tract of the left ventricle of the heart is the ascending aorta 101a. Segment 101b of the artery passes in front of trachea 103 and up towards the base of the neck, then arches 101c towards the lower part of the body.

The location of ascending aorta 101a, beneath the suprasternal notch 100a, provides access for an external BIA electrode, namely a fourth electrode 14 for the system, if necessary. An internal electrode 14 would be superior in signal quality but increase the complexity of the surgical requirements for monitoring by the placement of one additional internal electrode. A BIA measurement across ascending aorta 101a. First branches from the aorta are from aortic arch 101b, and the measurement of blood flow from ascending aorta 101a measures the volume of blood ejected from the left ventricle.

The ICOM system allows the continuous measurement of cardiac output from the two temporary pacing wires 20a and 20b placed in the peri-aortic adventitia. These ICOM wires and electrodes 20a, 20b, 14 are removed when the temporary pacing wires 22a, 22b, 24a, 24b are removed on postoperative days 4 or 5. These wires 20a, 20b, (22a or 22b), and 14 allow the measurement of impedance from the ascending aorta and the calculation of cardiac output.

Figure 3A:
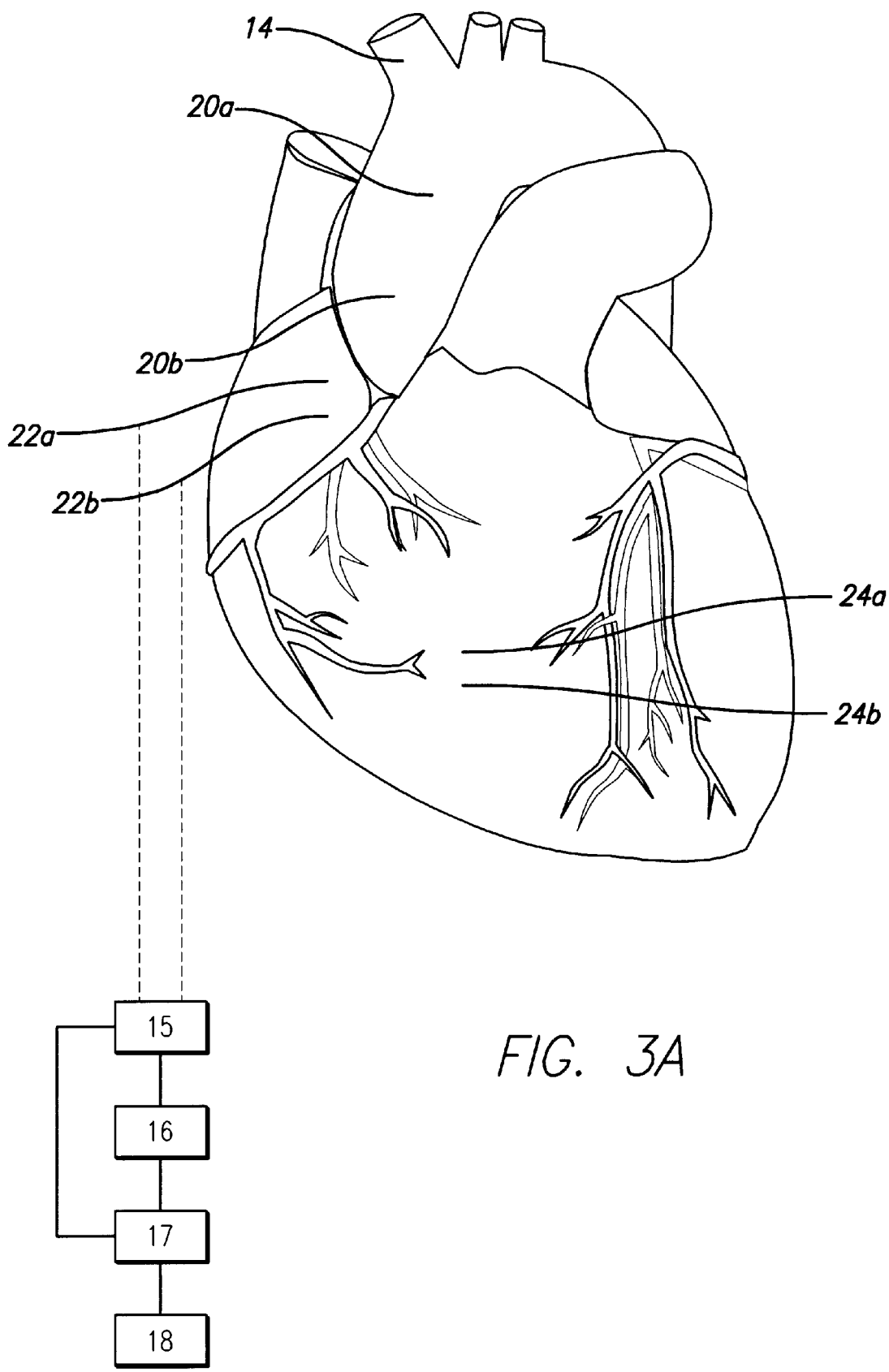
FIG. 3A is a vertical cross-sectional view of the cardiac region of a human showing a first arrangement of the electrodes of the apparatus of the present invention.
Figure 3B:
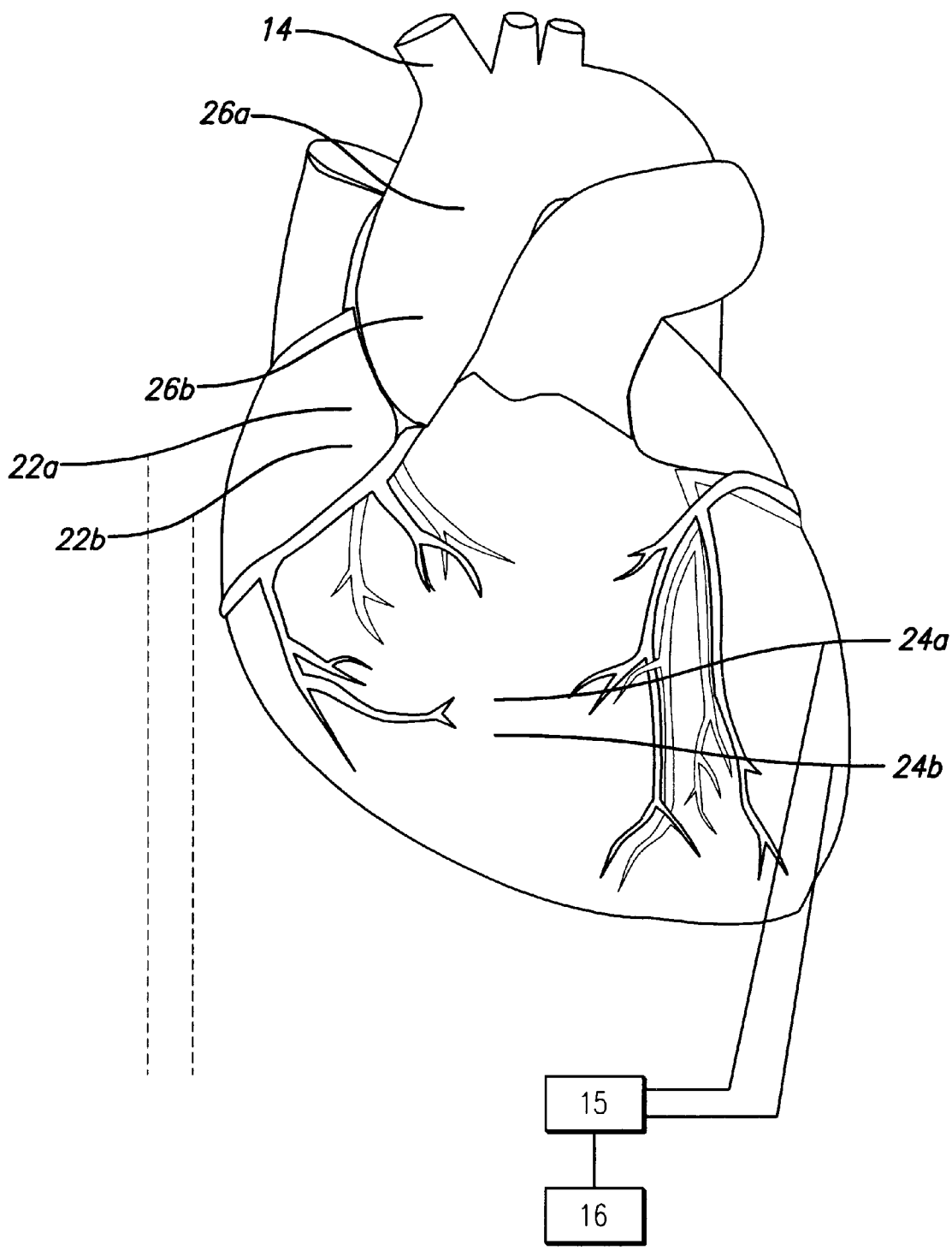
FIG. 3B is a vertical cross-sectional view of the cardiac region of a human showing a second arrangement of the electrodes of the apparatus of the present invention.

As shown in FIG. 3A, the two wires, 20a and 20b, namely for the first and second electrodes, are placed in the periaortic adventitia of the ascending aorta. The wires are placed more than about 10 mm apart, and orthogonal to flow as shown in FIG. 3A. In the alternative and/or additional configuration the wires and electrodes 26a and 26b are used and are in a parallel relationship relative to the flow as is shown in FIG. 3B.

The wires 20a, 20b and 26a and 26b are, for instance, stainless steel pacing wires with removable Teflon insulation. There is a cut away needle that allows placement in the tissue and a cuff of insulation at the tip that allows retention of the wire in place until external gentle pressure detaches the insulation and allows removal. There is a breakaway needle at the external end of the wire which allows placement through the chest wall. The break-away needle gives a connection to the circuitry without the sharp end remaining on the wire.

A sinusoidal current (2 ma 100 kHz) is injected into the atrial pacing leads, namely through the second electrodes (22a or 22b) and 14. Either (22a or 22b) or 14 can serve as ground. Frequencies between 1 kHz and 1 MHz would work. Lower frequencies of 10 to 20 kHz avoid cardiac stimulation and allow less expensive electronics. 100 kHz appears particularly effective, although there is no particular benefit to a specific frequency. Impedance measurements by impedance recorder 16 is effected between the two periaortic wires 20a and 20b and/or 26a and 26b. ECG for timing is obtained from the pacing wires 22a and 22b.

The impedance recorder 16 may be a commercially available impedance recorder providing both the sense current (generally less than 1 mA at a frequency of 50–100 kHz) and impedance measuring capability, for example the Minnesota Impedance Cardiograph Model 304A operating at 100 kHz or the Imagyn ECOM system. Signals output from the impedance recorder are digitally sampled by digital sampler 17, for example, at a rate of 400 Hz using a standard 20-bit analog to digital converter, available from ComputerBoards, Inc., Mansfield, Mass. The sampled output of digital sampler 17 is then provided to computer 18.

The ICOM system is useful for the intraoperative and postoperative monitoring of patients undergoing cardiac surgery. It is also useful for the design and development of internal thoracic impedance systems like the ECOM system.

An internal or external electrode 14, the ICOM source can be placed in the vicinity of the suprasternal notch for voltage pickup or on the aortic arch or pleura, and be electrically coupled to impedance recorder 16. The electrode 14 can comprise a spot EKG electrode, for example, the AMI 1750-001, manufactured by Medtronic-Andover Medical, Boston, Mass. Additional BIA measurements may be achieved using additional electrodes 14 spaced apart from one another in the vicinity of the suprasternal notch.

The algorithm for interpreting the electrical measurement can be simpler than the algorithm of the ECOM system. The main features can basically be the XCARDIA algorithm, namely the integral of DZ from BET to EET. Where DZ=Z(t)–Average Z(t). BET is beginning ejection time. EET is end ejection time. CO is cardiac output. HR is heart rate. M is an empirically derived proportionality constant. $CO=HR*m\int_{BET}^{EET}DZdt$ In other cases the algorithm can be as complex as the ECOM algorithm, illustrated in U.S. Pat. 5,791,349.

Electrodes 14, is the current source and electrode 22a or 22b is the ground. In an alternative embodiment, either 22a or 22b can be the source and 14 the ground. In a third embodiment electrode 14 can be an external electrode applied to the skin near the suprasternal notch. This position would place it in line with the ascending aorta. Internal electrodes are superior to any external electrodes.

Figure 4:
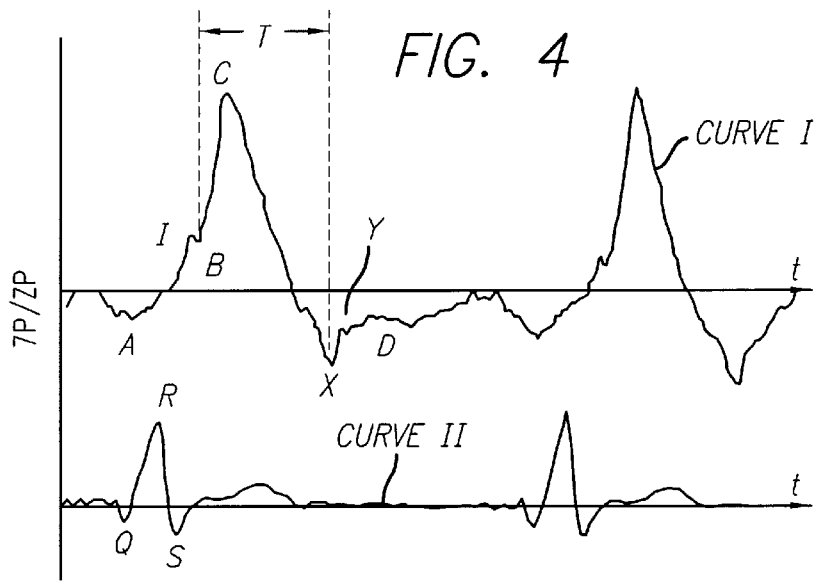
FIG. 4 is a graph showing the relationship between cardiac events and the first derivative of the measured bioelectrical impedance.

In FIG. 4, there is shown the first derivative of the measured impedance (dZ/dt) (curve I) is compared to a typical electrocardiograph waveform (curve II) for a normal patient, where the components of the waveform describing events within the cardiac cycle are labeled. Curve I includes an A-wave component, due to atrial activity at the beginning of the cardiac cycle, represented by a downward deflection in the curve. The I-wave component represents an upward deflection in curve I occurring during isometric contraction. The B-wave component corresponds to the start of blood flow out of the ventricles, while the C-wave component of curve I represents the major upward deflection during the cardiac cycle. The amplitude of this deflection measured from the zero point is used in the calculation of the ventricular stroke volume SV. The X and Y points of curve I reflect closure of the aorta and pulmonary valves, respectively. Point O corresponds to rapid filling of the ventricles. SV is calculated according to equation 3:

$$CO=HR*m\int_{BET}^{EET}DZdt \qquad (3)$$

where:
 CO=cardiac output
 HR=heart rate
 M=empirically derived proportionality constant
 EET=end ejection time
 BET=beginning ejection time
 DZ=change in impedance with time. Z(t) is the impedance signal with time. $\overline{Z(t)}$ is the average Z(t). DZ=Z(t)–$\overline{Z(t)}$ Cardiac output is computed for each data segment that is of good signal quality, i.e., where the amplitude of the change of the impedance signal is above a certain quality metric. The CO may be continuously updated on a display (not shown) associated with computer 18, and may consist of a running average of the cardiac output and a user-selectable number of preceding cardiac cycles. Stroke volume and heart rate can also be displayed.

Many variations of the ICOM are possible. Some of these are set out as follows.

i) The color of the ICOM wires can be distinct from the pacing wires to allow rapid identification and avoid confusion with the normal pacing wires.

ii) The orientation of the wires can be changed. Orthogonal is optimal but parallel also will work.

iii) The length of the wire exposed to the aortic adventitia can be shortened.

iv) The atrial and ventricular pacing wires can be used without the addition of any aortic wires. This modification requires a different computer algorithm for cardiac output calculation.

v) Conductivity dilution measurements can be made from the ICOM wires to check the calibration. Conductivity dilution is like thermal dilution. A fluid of known volume and RHO (conductivity) is injected and the change in conductivity with time recorded. A simple integration algorithm can calculate the true cardiac output.

vi) The cardiac volume can be measured from the ventricular pacing wires.

vii) Each ICOM lead can be dual electrode. This would allow the placement of two physical electrodes in the periaortic fat but four separate electrodes would be available for recording. This configuration would allow the simultaneous measurement of orthogonal and parallel impedance signals with only two physical electrodes in the aortic adventitia.

Advantages and improvements over existing systems include the following features:

i) The use of temporary pacing wires for bio-impedance measurements of cardiac output is an effective technique.
ii) Inexpensive.
iii) Accurate.
iv) Low risk.
v) Rapidly placed.
vi) Does not require an ICU bed or bed rest to maintain in place.
vii) Allows the development of other internal impedance devices, such as flow measurements in the superior vena cava.

The foregoing description of the preferred embodiments of the invention has been presented for the purposes of illustration and description. It is not intended to be exhaustive or to limit the invention to the precise form disclosed. Many modifications and variations are possible in light of the above teaching.

For instance other variations could include determining the cardiac output of a patient where at least one or more, and preferably the first two electrodes are located in a different locations relative to the aorta of a patient, but in a manner still directly operational in the sense of the scope of the invention. The exact placement of these two electrodes is not critical. Placement external to the pericardium, for example, is one of the alternative embodiments. The third electrode adapted to be disposed on the cardiac atrial area of the patient. A fourth electrode is either external on the body surface or internal on the aortic adventitia, pleura, or chest wall.

The bioelectrical impedance recorder measures voltages between the first two electrodes, and passes a current between the third and fourth electrodes. The output of the bioelectrical impedance recorder is used to compute a metric corresponding to the patient's cardiac output. Alternatively, the system can be produced with only two electrodes near the aorta serving both as recording and current source and ground. This embodiment is likely to be less stable and less accurate.

It is intended that the scope of the invention be limited not by this detailed description, but rather by the claims appended hereto.

What is claimed is:

1. Apparatus for determining the cardiac output of a patient comprising:
   at least two electrodes adapted to be relatively spaced apart and disposed in a relatively near location with the aorta of a patient;
   a third electrode adapted to be disposed on the cardiac atrial area of the patient;
   a fourth electrode located either externally on the body surface or internally; a bioelectrical impedance recorder for measuring voltages between the first two electrodes and for passing a current between the third and fourth electrodes; and
   means for processing the output of the bioelectrical impedance recorder to compute a metric corresponding to the patient's cardiac output.

2. The apparatus as claimed in claim 1 including a first and second electrodes coupled to the bioelectrical impedance recorder and disposed with the peri-aortic adventitia or fat pad.

3. Apparatus as claimed in claim 1 wherein the third electrodes are a pair of electrodes and are adapted to be cardiac pacing electrodes.

4. The apparatus as claimed in claim 3 wherein the fourth electrode is coupled to the bioelectrical impedance recorder and adapted to be disposed on the skin of the thorax in the vicinity of the suprasternal notch.

5. The apparatus as claimed in claim 1 further including a pacemaker controlling the heart rate of the patient, the pacemaker coupled to the means for processing and responsive to the metric corresponding to the cardiac output.

6. The apparatus as claimed in claim 5 wherein the third electrodes are electrodes of the cardiac pacemaker.

7. The apparatus as claimed in claim 1 wherein the means for processing further comprises circuitry for digitizing the output of the bioelectrical impedance recorder.

8. A method of measuring the cardiac output of a patient comprising the steps of:
   positioning first and second electrodes selectively with the peri-aortic adventitia or fat pad of the patient in the vicinity of the ascending aorta, or internally or externally to the pericardium;
   positioning a third electrode on the cardiac atrial area of the patient;
   positioning a fourth electrode on the pleura, ascending aorta, great vessels, chest wall, or externally on an area near the suprasternal notch;
   applying a voltage between the third and fourth electrodes so that a current flows through the tissues of the patient between the first and second electrodes; and
   detecting a voltage developed across the first and second electrodes caused by the current flowing in the tissues of the patient, the voltage varying in accordance with changes in the electrical impedance of the tissues.

9. The method as claimed in claim 8 wherein the steps of applying the voltage and detecting a voltage developed across the first and second electrodes are performed continuously.

10. The method as claimed in claim 9 comprising the steps of:
    providing a pacemaker electrically coupled to the heart of the patient to control heart rate; and
    adjusting the heart rate responsive to voltage developed across the first and second electrodes to optimize cardiac output.

11. The method as claimed in claim 10 wherein the step of adjusting the heart rate comprises a step of altering the heart rate to obtain a predetermined cardiac output.

12. The method of claim 9 wherein the first and second electrodes are formed by the electrodes of a cardiac pacemaker.

13. Apparatus for determining the cardiac output of a patient comprising:
    a multi electrode system with at least some electrodes being adapted to be disposed with the ventricular area of the heart of the patient;
    a bioelectrical impedance recorder coupled to first and second electrodes to pass a current between the electrodes where the multi electrode system is a two electrode system or where the multi electrode system is a four electrode system between the third and fourth electrodes;

means for processing the output of the bioelectrical impedance recorder to compute a metric corresponding to the patient's cardiac output; and at least some of the electrodes also being adapted to be cardiac pacing electrodes for a pacemaker for controlling the heart rate of the patient, and a pacemaker being coupled to the means for processing and responsive to the metric corresponding to the cardiac output.

14. Apparatus for determining the cardiac output of a patient comprising:

first and second electrodes adapted to be disposed with the atrial area of the heart of the patient;

a bioelectrical impedance recorder coupled to a third and fourth electrodes to pass a current between the third and fourth electrodes means for processing the output of the bioelectrical impedance recorder to compute a metric corresponding to the patient's cardiac output; and at least some of the electrodes also being adapted to be cardiac pacing electrodes for a pacemaker for controlling the heart rate of the patient, and a pacemaker being coupled to the means for processing and being responsive to the metric corresponding to the cardiac output.

15. Apparatus for determining the cardiac output of a patient comprising:

at least two electrodes adapted to be relatively spaced apart and disposed relatively near the pericardium;

a third electrode adapted to be disposed on the cardiac atrial area of the patient;

a fourth electrode located either selectively on the aortic adventitia, pleura, or chest wall;

a bioelectrical impedance recorder for measuring voltages between the first two electrodes and for passing a current between the third and fourth electrodes; and means for processing the output of the bioelectrical impedance recorder to compute a metric corresponding to the patient's cardiac output.

16. Apparatus for determining the cardiac output of a patient comprising:

at least two electrodes adapted to be relatively spaced apart and disposed relatively near the aorta;

a bioelectrical impedance recorder coupled to the at least two electrodes for measuring voltages between the two electrodes and for passing a current between the at least two electrodes; and means for processing the output of the bioelectrical impedance recorder to compute a metric corresponding to the patient's cardiac output.

17. The apparatus as claimed in claim 16 further including a pacemaker controlling the heart rate of the patient, the pacemaker coupled to the means for processing and responsive to the metric corresponding to the cardiac output.

18. Apparatus for determining the cardiac output of a patient comprising:

first electrodes adapted to be disposed with the peri-aortic adventitia or fat pad of the patient;

second electrodes adapted to be disposed on the cardiac atrial area of the patient;

a bioelectrical impedance recorder coupled to the first and second electrodes to pass a current between the electrodes; and means for processing the output of the bioelectrical impedance recorder to compute a metric corresponding to the patient's cardiac output.

19. Apparatus as claimed in claim 18 wherein each of the first electrodes and second electrodes includes a pair of electrodes, and including respectively wires connected to the respective electrodes.

20. Apparatus as claimed in claim 18 including further electrodes, the further electrodes are adapted also to be the cardiac pacing electrodes.

21. The apparatus as claimed in claim 18 including a further electrode coupled to the bioelectrical impedance recorder and adapted to be disposed on the skin of the thorax in the vicinity of the suprasternal notch.

22. A method of measuring the cardiac output of a patient comprising the steps of:

positioning first electrodes with the peri-aortic adventitia or fat pad of the patient in the vicinity of the ascending aorta;

positioning second electrodes on the cardiac atrial area of the patient;

applying a voltage between the first and second electrodes so that a current flows through the tissues of the patient between the first and second electrodes; and detecting a voltage developed across the first and second electrodes caused by the current flowing in the tissues of the patient, the voltage varying in accordance with changes in the electrical impedance of the tissues.

23. The method as claimed in claim 22 wherein the steps of applying the voltage and detecting a voltage developed across the first and second electrodes are performed continuously.

24. The method as claimed in claim 23 comprising the steps of:

providing a pacemaker electrically coupled to the heart of the patient to control heart rate; and adjusting the heart rate responsive to voltage developed across the first and second electrodes to optimize cardiac output.

25. The method as claimed in claim 24 wherein the step of adjusting the heart rate comprises a step of lowering the heart rate to obtain either a predetermined minimum hear rate or until the cardiac output is measured to be decreasing.

26. The method as claimed in claim 25 wherein the step of lowering the heart rate includes adjusting the heart rate downward by two beats per minute every 60 seconds.

27. The method of claim 22 wherein the second electrodes are the formed by the electrodes of a cardiac pacemaker.

28. Apparatus for determining the cardiac output of a patient comprising:

at least two electrodes adapted to be relatively spaced apart near the location of a patient;

a third electrode adapted to be disposed on the cardiac atrial area of the patient;

a fourth electrode located either externally on the body surface or internally;

a bioelectrical impedance recorder for measuring voltages between the first two electrodes and for passing a current between the third and fourth electrodes; and means for processing the output of the bioelectrical impedance recorder to compute a metric corresponding to the patient's cardiac output;

at least some of the electrodes also being adapted to be cardiac pacing electrodes for a pacemaker for controlling the heart rate of the patient, and a pacemaker being coupled to the means for processing and being responsive to the metric corresponding to the cardiac output.

29. The apparatus as claimed in claim 28 wherein the means for processing further comprises circuitry for digitizing the output of the bioelectrical impedance recorder.

30. Apparatus as claimed in claim 28 wherein the third electrode is a pair of electrodes and the pair of electrodes is adapted to be the cardiac pacing electrodes.

31. The apparatus as claimed in claim 30 wherein the fourth electrode is coupled to the bioelectrical impedance recorder and adapted to be disposed on the skin of the thorax in the vicinity of the suprasternal notch.

32. Apparatus for determining the cardiac output of a patient comprising:
- first and second electrodes adapted to be disposed with the peri-aortic adventitia or fat pad of the patient or internally or externally to the pericardium;
- a bioelectrical impedance recorder coupled to a third and fourth electrodes to pass a current between the third and fourth electrodes;
- means for processing the output of the bioelectrical impedance recorder to compute a metric corresponding to the patient's cardiac output; and
- at least some of the electrodes also being adapted to be cardiac pacing electrodes for a pacemaker for controlling the heart rate of the patient, and a pacemaker being coupled to the means for processing and being responsive to the metric corresponding to the cardiac output.

33. Apparatus for determining the cardiac output of a patient comprising:
- at least two electrodes adapted to be relatively spaced apart and disposed relatively near the aorta of a patient, located at a distance more proximate to the aorta than the inner wall of the trachea or esophagus;
- a third electrode adapted to be disposed on the cardiac atrial area of the patient;
- a fourth electrode located either externally on the body surface or internally; a bioelectrical impedance recorder for measuring voltages between the first two electrodes and for passing a current between the third and fourth electrodes; and
- means for processing the output of the bioelectrical impedance recorder to compute a metric corresponding to the patient's cardiac output.

34. The apparatus as claimed in claim 33 wherein the fourth electrode is coupled to the bioelectrical impedance recorder and adapted to be disposed on the skin of the thorax in the vicinity of the suprasternal notch.

35. The apparatus as claimed in claim 33 further including a pacemaker controlling the heart rate of the patient, the pacemaker coupled to the means for processing and responsive to the metric corresponding to the cardiac output.

36. The apparatus as claimed in claim 33 wherein the means for processing further comprises circuitry for digitizing the output of the bioelectrical impedance recorder.

37. Apparatus as claimed in claim 33 wherein the third electrodes are a pair of electrodes and are adapted to be cardiac pacing electrodes.

38. The apparatus as claimed in claim 37 wherein the third electrodes are electrodes of the cardiac pacemaker.

39. Apparatus for determining the cardiac output of a patient comprising:
- at least two electrodes adapted to be relatively spaced apart and disposed relatively near the aorta, located at a distance more proximate to the aorta than the inner wall of the trachea or esophagus;
- a bioelectrical impedance recorder coupled to the at least two electrodes for measuring voltages between the two electrodes and for passing a current between the at least two electrodes; and
- means for processing the output of the bioelectrical impedance recorder to compute a metric corresponding to the patient's cardiac output.

\* \* \* \* \*